United States Patent [19]

Hepner et al.

[11] Patent Number: 5,391,263
[45] Date of Patent: Feb. 21, 1995

[54] PROCESS FOR THE SEPARATION OF GLYCOLS FROM DIMETHYL TEREPHTHALATE

[75] Inventors: Richard R. Hepner; Robert E. Michel, both of Wilmington, N.C.; Robert E. Trotter, Hockessin, Del.

[73] Assignee: E. I. Du Pont de Nemours and Company, Wilmington, Del.

[21] Appl. No.: 186,088

[22] Filed: Jan. 26, 1994

[51] Int. Cl.6 .................................. B01D 3/36
[52] U.S. Cl. ........................... 203/51; 203/60; 203/71; 560/78; 568/868; 568/871
[58] Field of Search ............ 203/51, 60, 71, DIG. 23, 203/38; 560/78; 568/868, 871

[56] References Cited

U.S. PATENT DOCUMENTS

| | | | |
|---|---|---|---|
| 3,227,743 | 1/1966 | Shaw et al. | 203/60 |
| 4,028,195 | 6/1977 | Becker et al. | 203/38 |
| 4,057,471 | 11/1977 | Chueh | 568/868 |
| 4,151,048 | 4/1979 | Becker et al. | 568/868 |

FOREIGN PATENT DOCUMENTS 3302127  7/1984  Germany .

Primary Examiner—Virginia Manoharan

[57] ABSTRACT

Separation of ethylene glycol and diethylene glycol from dimethyl terephthalate is accomplished by distillation using methyl benzoate or the methyl ester of p-toluic acid as an azeotropic agent.

2 Claims, 1 Drawing Sheet

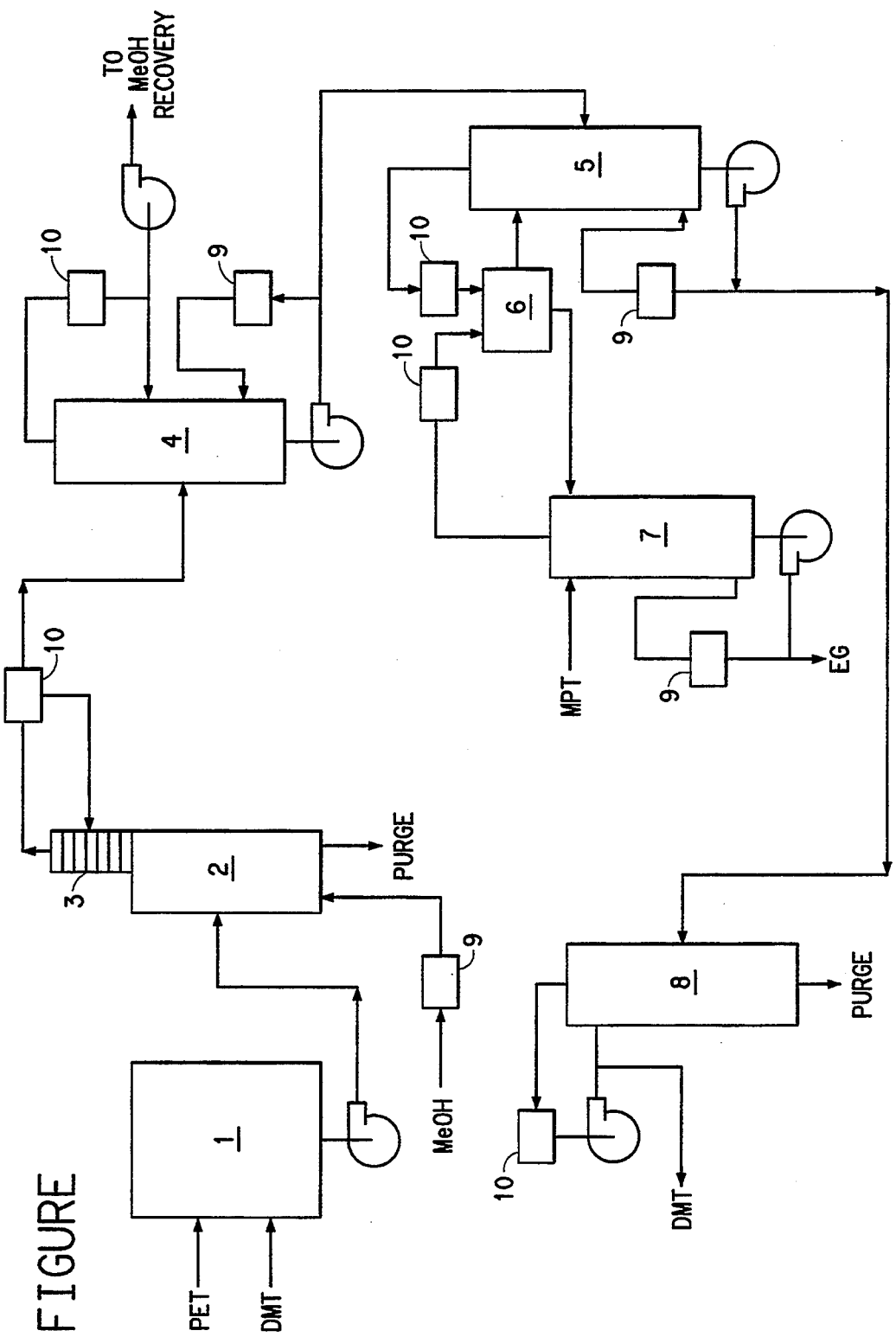
FIGURE

PROCESS FOR THE SEPARATION OF GLYCOLS FROM DIMETHYL TEREPHTHALATE

FIELD OF THE INVENTION

This invention relates to the separation of glycols from dimethyl terephthalate, and more particularly to the separation of glycols and dimethyl terephthalate from a mixture formed by the treatment of waste polyester with methanol to form dimethyl terephthalate, ethylene glycol and diethylene glycol.

BACKGROUND OF THE INVENTION

Published European Patent application 0,484,963 A3 (published May, 13, 1992) discloses a process for the depolymerization of polyester waste with methanol vapor to form dimethyl terephthalate and ethylene glycol. Solvent may also be present in the depolymerization zone. U.S. Pat. No. 4,057,471 to Chueh discloses the separation of alkylene glycols from azeotropic mixtures containing lower carboxylate esters of alkylene glycols by adding an azeotroping agent effective to form a minimum-boiling azeotrope with the glycol and then distilling the newly formed mixture.

SUMMARY OF THE INVENTION

The present invention is a process for the recovery of dimethyl terephthalate and ethylene glycol and diethylene glycol from a mixture of azeotropes of ethylene glycol with dimethyl terephthalate and diethylene glycol with dimethyl terephthalate which comprises: adding an azeotropic agent selected from the group consisting of the methyl ester of p-toluic acid (i.e. methyl p-toluate), methyl benzoate, and mixtures of the methyl ester of p-toluic acid and methyl benzoate to the mixture in an amount sufficient to form new azeotropes and then distilling the new azeotropes from the resulting mixture and recovering as bottoms dimethyl terephthalate, cooling the distillate and allowing the azeotropes to separate into two phases, namely a phase rich in the azeotropic agent, and a phase rich in ethylene glycol and diethylene glycol, and separating the two phases. Preferably the two phases are separated by decantation.

BRIEF DESCRIPTION OF THE DRAWING

The FIGURE is a diagrammatic view of system of recovery of ethylene glycol and dimethyl terephthalate from polyester waste including the azeotropic distillation system of the invention.

DETAILED DESCRIPTION

When waste polyester is depolymerized by the use of methanol vapor, ethylene glycol and diethylene glycol form low boiling azeotropes with dimethyl terephthalate. These glycols cannot be cleanly separated from dimethyl terephthalate by ordinary distillation. However, ethylene glycol and diethylene glycol can be cleanly separated from dimethyl terephthalate by removing the glycols by distillation as low boiling azeotropes with the methyl ester of p-toluic acid or with methyl benzoate or with mixtures of the methyl ester of p-toluic acid and methyl benzoate. The newly formed azeotrope distills overhead and the dimethyl terephthalate is recovered as bottoms. On cooling, the overhead mixture separates into two liquid phases: a phase rich in the methyl ester of p-toluic acid or methyl benzoate and a phase rich in the glycol. The two phases can be separated, for example by decantation, and the phase rich in the azeotropic agent can be recycled to the distillation column.

Referring to the drawing, polyethylene terephthalate (PET) and dimethyl terephthalate (DMT) (serving as a solvent) are fed into a heated vessel 1, where PET is melted. The molten polymer mixture is then fed to reactor 2, where it is treated with methanol vapor and depolymerized by the action of methanol vapor. From the reflux section 3 of the reactor 2, a vapor mixture of methanol, ethylene glycol, dimethyl terephthalate, and diethylene glycol is passed to methanol removal column 4. After removal of methanol, the mixture is passed to azeotrope column 5 where the mixture is treated with an azeotropic agent selected from the group consisting of the methyl ester of p-toluic acid (MPT), methyl benzoate, and mixtures of these agents. The ethylene glycol azeotrope and the diethylene glycol azeotrope are taken over head, and the dimethyl terephthalate is removed from column 5 as bottoms. The overhead mixture is passed to vessel 6 where it is allowed to separate into two phases, namely a phase rich in the azeotropic agent and a phase rich in the glycols. The azeotropic rich phase may be recycled to column 5. The phase rich in glycols is passed to distillation column 7, where the azeotropic agent present in this phase is recovered overhead, and the glycols (EG) recovered as bottoms. The azeotropic agent ultimately used in column 5 is initially fed to column 7 where impurities are removed. The bottoms from column 5 are passed to distillation column 8 where dimethyl terephthalate is taken overhead. In the drawing various heaters are designated 9 and various condensers designated 10.

EXAMPLES

A small scale continuous distillation column having 15 trays was used in these examples. The distillation pot was charged as indicated in the Table, and after the had reached equilibration, feed was started with the indicated composition and rate. The results are shown in the table.

| COMPOSITIONS AND RUN CONDITIONS | | | | | | | | | | | | | |
|---|---|---|---|---|---|---|---|---|---|---|---|---|---|
| | Init. Charge | | | | Feed Composition (1) | | | | | | | | |
| Run | Grams | DMT % | MB % | MPT % | Grams | DMT % | EG % | DEG % | MB % | MPT % | MFB % | MHET % | Feed Rate g/min. |
| 1 | 135 | 74 | 0 | 26 | 242 | 50 | 30 | 0 | 0 | 20 | 0 | 0 | 1.9 |
| 2 | 135 | 74 | 0 | 26 | 470 | 47.6 | 28.6 | 4.8 | 0 | 19 | 0 | 0 | 2 |
| 3 | 135 | 74 | 0 | 26 | 629 | 52.6 | 15.8 | 0 | 19 | 8.9 | .06 | 0 | 2.5 |
| 4 | 126 | 79 | 14 | 6.6 | 575 | 47.8 | 14.5 | 1.3 | 22 | 10 | .07 | 0 | 2.3 |
| 5 | 76 | 65 | 24 | 11 | 563 | 48.2 | 16 | 1.3 | 21 | 9.4 | 0.7 | 0 | 1.8 |
| 6 | 100 | 50 | 50 | 0 | 546 | 48.2 | 16 | 2 | 344 | 0 | 0 | 0 | 2.5 |
| 7 | 120 | 42 | 0 | 58 | 436 | 35.8 | 23 | .09 | 0 | 40 | 0 | 8.9 | 1.0 |

| Initial Overh'd | | Total Overhead Composition | | | | | |
|---|---|---|---|---|---|---|---|
| MB | MPT | DMT | EG | DEG | MB | MPT | MFB MHET |

-continued

| COMPOSITIONS AND RUN CONDITIONS | | | | | | | | | | | |
|---|---|---|---|---|---|---|---|---|---|---|---|
| Run | Grams | % | % | Grams | % | % | % | % | % | % | % |
| 1 | NA | | | 149.5 | 1.4 | 43 | 0 | 0 | 56.1 | 0 | 0 |
| 2 | 26.7 | 0 | 100 | 188.3 | 2 | 34 | 9.2 | 0 | 54 | 0 | 0 |
| 3 | 29.4 | 0 | 100 | 244.4 | 0.4 | 34 | 0 | 40 | 25 | 0 | 0 |
| 4 | 22 | 85 | 15 | 251.3 | 0 | 31 | 0 | 30 | 24 | 0 | 0 |
| 5 | 38.3 | 72 | 27 | 250.8 | 0.5 | 33 | 2.1 | 41 | 23 | 0 | 0 |
| 6 | 42 | 100 | 0 | 256 | 0.9 | 33 | 0 | 66 | 0 | 0 | 0 |
| 7 | 39 | 0 | 100 | 312 | 0 | 33 | 0 | 0 | 67 | 0 | 0 |

| Pot Compositions (From Samples) | | | | | | | | |
|---|---|---|---|---|---|---|---|---|
| Run | Grams | DMT | EG | DEG | MB | MPT | MFB | MHET |
| 1 | 216 | 99 | 0 | 0 | 0 | .04 | 0 | 0 |
| 2 | 308 | 99 | 0 | .12 | 0 | .04 | 0 | 0 |
| 3 | 417 | 99 | 0 | 0 | 0 | .12 | .07 | 0 |
| 4 | 358 | 99 | 0 | .08 | 0 | .02 | .11 | 0 |
| 5 | 314 | 99 | 0 | 0 | 0 | 0 | .07 | 0 |
| 6 | 304 | 97 | 0 | 2.8 | 0 | 0 | 0 | 0 |
| 7 | 295 | 86 | 0 | 0 | 0 | 0 | 0 | 14 |

(1) DMT = dimethylterephthalate, EG = ethylene glycol, DEG = diethylene glycol, MB = methyl benzoate, MPT = methyl p-toluate, MFB = methyl p-formylbenzoate, MHET = methyl hydroxyethylterephthalate.

What is claimed is:

1. A process for the recovery of dimethyl terephthalate, ethylene glycol and diethylene glycol from a mixture of azeotropes of ethylene glycol with dimethyl terephthalate and diethylene glycol with dimethyl terephthalate which comprises: adding an azeotropic agent selected from the group consisting of the methyl ester of p-toluic acid, methyl benzoate, and mixtures of the methyl ester of p-toluic acid and methyl benzoate to the mixture of azeotropes in an amount sufficient to form new azeotropes and then distilling the new azeotropes from the resulting mixture and recovering as bottoms dimethyl terephthalate, cooling the distillate and allowing the azeotropes to separate into two phases, namely a phase rich in the azeotropic agent, and a phase rich in ethylene glycol and diethylene glycol, and separating the two phases.

2. The process of claim 1 in which the two phases are separated by decantation.

* * * * *